United States Patent [19]
Kratzer et al.

[11] Patent Number: 5,035,693
[45] Date of Patent: Jul. 30, 1991

[54] DEVICE FOR SELECTIVE DESTRUCTION OF CELLS

[76] Inventors: Michael Kratzer, Leopoldstrasse 56, D-8000 Munchen 40; Eberhard Unsöld, Dr. Hofmeisterstrasse 16a, D-8042 Oberscheissheim, both of Fed. Rep. of Germany

[21] Appl. No.: 167,211

[22] Filed: Mar. 11, 1988

[30] Foreign Application Priority Data

Mar. 16, 1987 [DE] Fed. Rep. of Germany ....... 3708511

[51] Int. Cl.$^5$ ............................................. A61M 5/01
[52] U.S. Cl. ..................................... 606/12; 128/396; 604/5
[58] Field of Search ................ 128/395, 396, 6, 303.1, 128/654; 209/38; 350/484, 486, 6.3, 6.4; 424/95, 577; 604/4–6; 606/10–12

[56] References Cited

U.S. PATENT DOCUMENTS

| | | | |
|---|---|---|---|
| 3,883,683 | 5/1975 | Pardes | 350/6.3 |
| 4,316,467 | 2/1982 | Muckerheide | 606/12 |
| 4,395,397 | 7/1983 | Shapiro | 424/95 |
| 4,538,613 | 4/1985 | Rosenberg | 128/6 |
| 4,564,012 | 1/1986 | Shimada | 128/395 |
| 4,640,573 | 2/1987 | Kataoka et al. | 350/6.3 |
| 4,641,650 | 2/1987 | Mok | 606/12 |
| 4,683,889 | 8/1987 | Edelson | 128/395 |

FOREIGN PATENT DOCUMENTS

| | | | |
|---|---|---|---|
| 1408571 | 4/1971 | Japan | 350/6.3 |
| 0005744 | 1/1979 | Japan | 350/6.3 |

OTHER PUBLICATIONS

Bartz et al, "Simultaneous Dual Scanner" 4/71.
Shogren "Scanning System for Copier" 12/81.

*Primary Examiner*—Edward M. Coven
*Assistant Examiner*—Mark S. Graham

[57] ABSTRACT

Apparatus for selective destruction or inactivation of cells is disclosed wherein cells are arrayed in a plane for successive illumination, by optical X-Y scanning devices, with a first low power red light beam to produce in particular cells certain radiations responsive to the illumination. These response radiations are detected and used to enable a second higher powered light beam directed through substantially the same optical scanning paths, to destroy or inactivate the cells producing the response radiations. The illumination, response, detection, and high power radiation steps are accomplished by devices acting in times short as compared to the X-Y scanning devices so as to make the accurate treatment of each of large numbers of cells highly effective. Alternate embodiments disclose the use of a signal laser light source to selectively provide both the low and high powered light beams, various X-Y scanning arrangements, and various devices for correcting the spherical aberration of the scanned beams in variously positioned image planes.

13 Claims, 2 Drawing Sheets

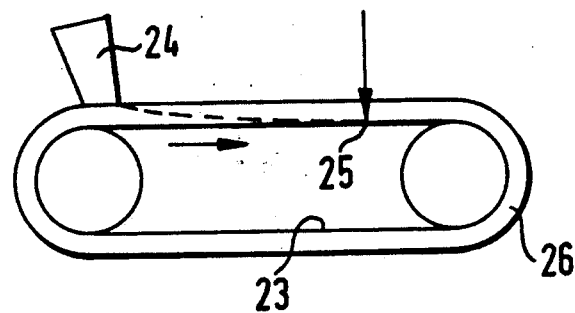
FIG. 3
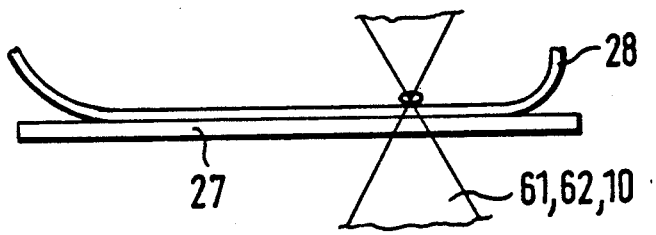
FIG. 4
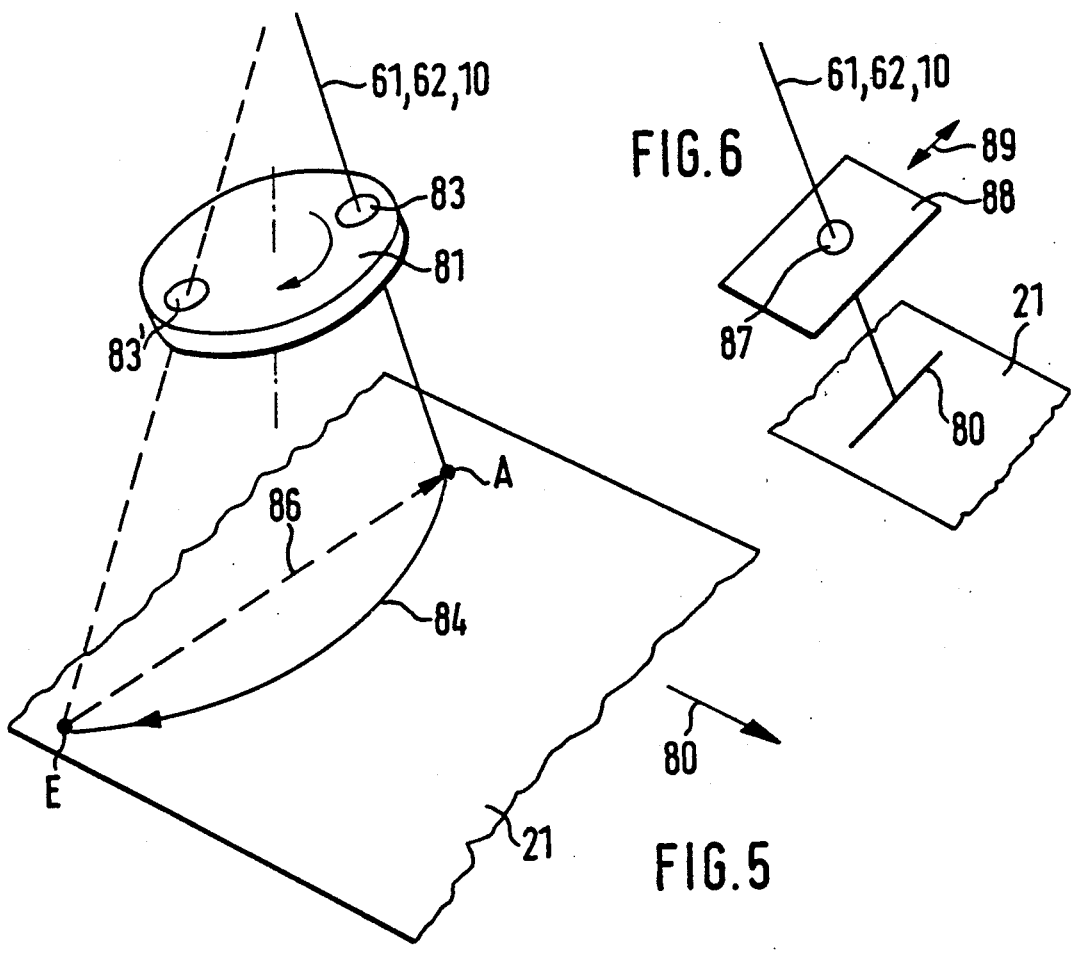
FIG. 6
FIG. 5

DEVICE FOR SELECTIVE DESTRUCTION OF CELLS

BACKGROUND OF THE INVENTION

1. Field of the Invention

The present invention relates generally to apparatus for the selective destruction of cells, and more particularly to a system of the type wherein cells arrayed in a plane are successively illuminated with a low powered light beam and examined for particular radiation resulting from this illumination to selectively enable a high powered beam to accomplish the destruction of particular cells.

2. Description of the Prior Art

From the German patent document DE-OS 53 31 969, a flow cytometry device is known for detection of interesting biological particles in a sample of unknown particles, in which a beam from a light source is directed onto the particles, and light related data is detected by a measuring device if the light beam strikes a particle. In this case the measuring device detects, inter alia, the fluorescence emitted by certain particles.

From the German patent document DE-PS 33 31 017, a process is disclosed for distinguishing various types of cell subpopulations, in which antibody proteins are labeled with fluorochromes; the labeled antibody proteins are combined with a sample of cells, in which specific receptors for the labeled antibody proteins are suspected; the fluorochromes are stimulated by suitable techniques and the cells are analyzed for classification on the basis of emitted fluorescence.

SUMMARY OF THE INVENTION

It is a primary object of the present invention to provide apparatus in which cells, especially blood cells, are optically characterized and selectively destroyed with light beams to achieve a therapy or to study the interaction of blood cells.

A substantial advantage of the present invention is that it now becomes possible, depending on specific syndromes or problems, to selectively destroy cells, especially blood cells negatively influencing or causing the syndrome, and in this way to achieve an improvement in or assist in the healing of the pathological process. Preferably this can take place like a blood washing, by the blood being branched off from the patient's body and fed to the device according to the present invention. Within the device, the blood cells causing or influencing the disease, in which, for example, certain lymphocyte populations are involved, are selectively destroyed, and the blood is then reintroduced into the blood circulation of the patient. By destruction of these blood cells the symptoms of the disease tend to be improved, or healing is assisted. Especially, it is possible that with the help of the device according to the present invention diseases such as leukemias, rejection phenomena in transplants, AIDS and autoimmune diseases can also be effectively treated.

A substantial advantage of the device according to the invention is that syndromes, especially the above mentioned syndromes, can be treated without the patient's health being endangered by side effects, as in the case, for example, in chemotherapy.

In an advantageous way the invention makes it possible for different syndromes to be treated with one and the same device, and only depending on the disease to be treated, the use of characteristic properties of the individual blood cells or the use of different antibody RNA samples or other labeling materials is necessary.

This device can advantageously be used both for treatment of static blood and flowing blood. It is also possible with this device to treat cell suspensions on a large scale.

The invention is also advantageously used for purification of biotechnologically usable cell suspensions. In addition, this device can also advantageously be used in the field of chromosome analytic separation of cells.

Another advantage is that the device according to the invention can substantially be produced from components available on the market.

In a preferred embodiment, and by means of alternate embodiments, the present invention discloses apparatus for providing the above advantages by carrying out the following steps. In this illustrative case, blood is used as "cell suspension" to assist in the explanation.

(1) A patient's blood is branched from the circulation by, illustratively, an extracorporeal circulation.

(2) An individual cell group, e.g., erythrocytes, leukocytes, lymphocytes or thrombocytes, is taken from the blood by a cell selection unit, since it can contain relevant cells for certain syndromes. The rest of the blood cells are fed back into the blood circulation by a cell feed device.

(3) The removed group contains cells that are relevant and irrelevant for the syndrome, cells which cannot be distinguished from one another morphologically and physically. For this reason, selection of the relevant blood cells takes place by use of fluorescent antibodies, DNA samples, RNA samples or other labeling means directly or indirectly.

(4) All blood cells of the blood cell group are brought by a scanning device into the focal or image plane of an optical system and are successively illuminated with a light beam with a power harmless to the blood cells. Because of their labeling, the relevant blood cells emit a fluorescence.

(5) The light emitted by the labeled blood cells is detected by a sensor within a detector unit.

(6) By radiation of a light beam within an active unit, with a higher power which is sufficient for destruction of the blood cells, into the optical system, labeled or relevant cells, which are responsible for the syndrome, can be destroyed. In this case, the light beam with the higher power is activated in that the fluorescence of the labeled or relevant cells, after their stimulation by the light beam with low power, is detected for generation of an activation signal.

BRIEF DESCRIPTION OF THE DRAWINGS

Additional objects and advantages of the invention will become apparent to those skilled in the art as the description proceeds with reference to the accompanying drawings wherein:

FIG. 3 shows a simplified side view of a belt conveyor employed in an embodiment of the present invention;

FIG. 4 shows a simplified cross-sectional view of an alternate embodiment image plane arrangement;

FIG. 5 diagrammatically shows a first spherical aberration correction technique for use in the present invention; and FIG. 6 diagrammatically shows an alternate spherical aberration technique.

DETAILED DESCRIPTION OF THE PREFERRED EMBODIMENT

Figure 1:
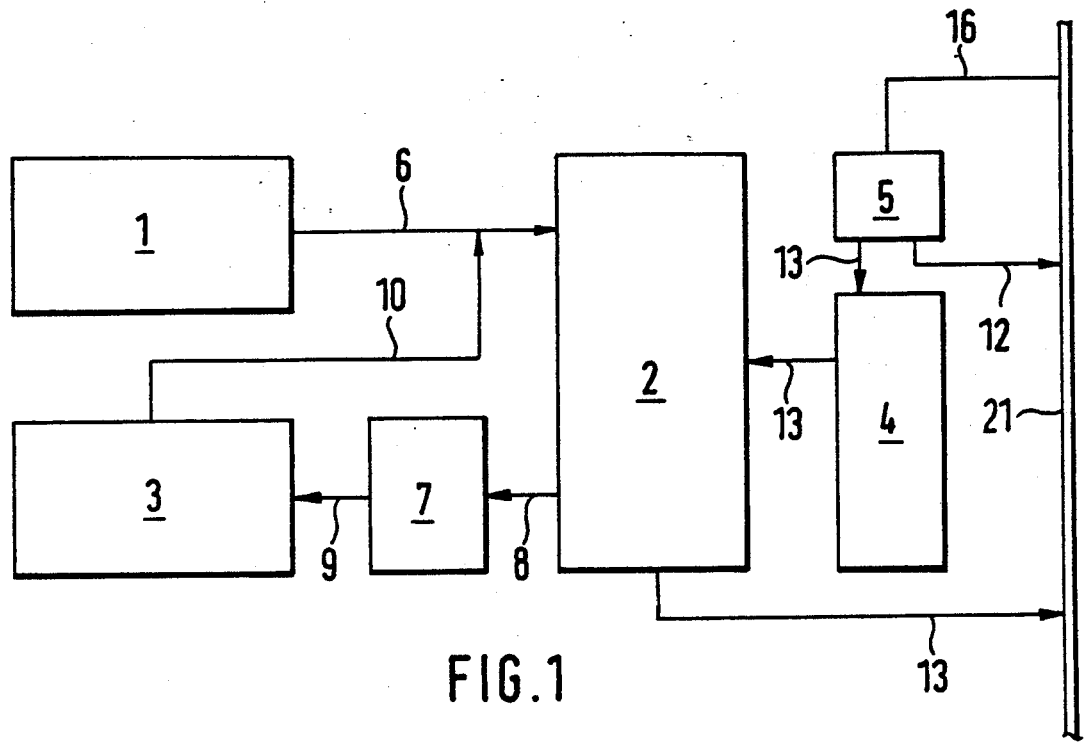
FIG. 1 is a simplified block diagram outlining the overall sequence of operation of the system according to the present invention.

Operation of the present invention is first explained in general terms in connection with the simplified block diagram of FIG. 1. In FIG. 1, the device according to the present invention is shown as consisting substantially of an analysis unit 1, a scanning device 2, an active unit 3, a cell feed device 4, and a detector unit 7. In this arrangement, the cell feed device 4 can suitably be connected upstream from a cell preselector 5.

The analysis unit 1 produces at least one light beam 6 with a power harmless to cells, especially for blood cells. This light beam 6 is projected by the scanning device 2 onto an image plane of an optical system and is advantageously scanned there in two directions (X and Y of a Cartesian coordinate system) if the image plane itself is stationary; or is scanned only in one direction of such coordinate system, while the image plane is moved in the other direction. Alternatively, it is also possible for the light beam 6 to be projected only onto the image plane by the scanning device 2, and only the image plane is moved in a preset direction, so that no surface, as in the two preceding scanning cases, but only a line is scanned by the light beam 6.

The detector unit 7 detects the fluorescence emitted by individual cells successively stimulated by light beam 6 in the image plane and/or the light radiation reflected on these cells and/or the radiation scattered on these cells and/or the radiation emitted by the cells. In FIG. 1 said emitted fluorescence and other response light beams are identified by the path 8. The detector unit 7 generates at least one detector signal 9, which corresponds to the detected emission and/or certain scattered or reflected radiation 8.

At least one detector signal 9 is applied to control devices within active unit 3, and an activation signal is generated which activates a light source contained in active section 3. This light source produces power light beam 10, whose power is so high that it is sufficient for destroying or inactivating cells. This power light beam 10 is preferably fed to the optical system of scanning device 2, so that it is projected on the same point of the image plane as was light beam 6. This means that with stimulation of a cell by light beam 6 and with reception of a predetermined fluorescence emitted by this cell, or of a predetermined radiation reflected or scattered on this cell, the activation signal and power light beam 10 are produced; since in the case of the cell a labeled relevant cell responsible for a syndrome is involved. This cell is then destroyed by the power light beam 10. It is also possible for the analysis steps (projection of light beam 6) and the steps of active intervention (power light beam 10) to be performed separately in space and time.

The cell feed device 4 feeds the cells to be examined or treated into an image plane within scanning device 2. In this case the fed cells, if blood cells are involved, can be taken via pathway 16 from a patient's blood circulation 11 as shown diagrammatically, and can be fed back in this blood circulation after therapy or examination has been performed. In the case shown, cell preselector 5 can be used. It draws out from the blood fed to it, illustratively by a centrifugal operation, an individual cell group, which may contain the cells relevant for the syndrome to be treated. In this case, only the removed relevant blood cells are brought by the cell feed device 4 into the image plane of the scanning device 2. The remaining blood cells of the blood branched off from the blood circulation 11 are fed back to it immediately after cell preselector 5 via pathway 12, while the treated blood cells are fed back into the blood circulation 11 from the image plane via pathway 13. By means of this preselection, not all the blood cells of the blood supply but only the blood cells of an individual cell group, in which preferably the cells responsible for the syndrome to be treated are contained, must be scanned. Consequently, the entire scanning procedure can be substantially accelerated.

Preferred embodiments of this invention are now explained in more detail in connection with FIG. 2. Elements shown in FIG. 2 which were explained in connection with FIG. 1 are correspondingly designated.

In the analysis unit 1, a laser source is preferably used as a light source 51, since in this case a particularly sharp and small focal spot can be produced in an image plane 21 of the scanning device 2. This leads, for example, to the production of well defined fluorescences of the cells successively scanned in the image plane 21.

An argon laser is particularly well suited as laser light source 51, whose stimulation frequency corresponds, illustratively, to 488 nm. Antibodies labeled with fluorescein isothiocyanate, if they are stimulated with 488 nm of the corresponding stimulation frequency, then emit a fluorescence at 550 nm. With laser sources, focal spots can easily be produced whose diameter is about 10 microns or less.

Instead of a single light source 51, several light sources can be provided, e.g., two light sources 51 and 52, which produce light beams 61 and 62, respectively, whose power is harmless to the cells. When two light sources 51 and 52 are used, the cells can be stimulated in the image plane 21 at the same time with different frequencies so that, for example, two fluorescences with different wavelengths are produced. This can be advantageous for special problems or therapy. Moreover, this can be especially important for generation of trouble-free detector signals 9, since, by subtraction of the two signals detected by corresponding sensors of detector unit 7, in which fluorescence signals, illustratively, are involved, background signals can be eliminated.

The two light beams 61 and 62 are brought together into one beam and are picked up together by the optical system of scanning device 2. The optical system of scanning device 2 projects a focal spot of light source 51, or light sources 51 and 52, onto the image plane 21. Scanning device 2 includes two deflection mirrors 57 and 58, known in the art, one of which is shifted by a drive device for the deflection in an X direction, and the other is shifted by another drive device for deflection in a Y direction while oscillating. Instead of deflection mirrors 57 and 58, so-called electrooptical deflectors can alternatively be provided, which also are known in the art. In addition, deflection in the X and Y directions can be achieved in a way known in the art by other rotating optical means.

By using only one deflection mirror or only one electrooptical deflector, the deflection of light beam 61 or light beams 61 and 62 can occur in only one direction (for example, in the X direction). In this arrangement there is the possibility that image plane 21 itself may be moved in the other direction (for example, in the Y direction). This can suitably take place by means of a belt conveyor 22. In this arrangement, the image plane corresponds to a part of the surface of belt 23 and the deflection of light beam 61, or light beams 61 and 62, preferably takes place perpendicular to the direction of movement of the belt 23. By providing a transparent belt 23, a sensor device 71 of detector unit 7, which is explained below in greater detail, can be provided on the side of belt 23 opposite image plane 21. In case of use of a belt conveyor 22, the blood from a suitable storage 24 is properly put on the surface of belt 23 together with nutrient medium that keeps the blood cells alive; viewed in the direction of movement of belt 23, before the place on which light beam 61, or beams 61 and 62, is scanned.

Referring now to FIG. 3, an illustrative belt conveyor device is described in which the blood is put on one end of belt 23, and in which the blood cells during the movement of belt 23 to a scanning site 25 are so settled that they are placed exactly at scanning site 25 in the image plane on the belt surface. To achieve this, the rate of movement of belt 23 is set as a function of the settling process. To prevent lateral flowing off of the blood from belt 23, the belt includes side walls 26, so that the belt surface corresponds to the bottom of a formed, approximately U-shaped duct.

In a preferred alternate embodiment of the present invention as shown in FIG. 4, the image plane is formed by the surface of a transparent plate 27 and the scanning device 2 is alternately configured so that light beam 61, or beams 61 and 62, impact from below onto the plate 27. Then the blood which may be contained in a transparent plastic bag 28, or the like, or the blood cells selected by cell preselector 5 contained in the bag 28 can be placed on the opposite surface of plate 27. In this alternate embodiment, light beam 61, or beams 61 and 62, are focused on the plane of the cells resting on the bottom of bag 28. In this case, it is advantageous that the power light beam 10 focused on the individual cells with power leading to the destruction of relevant cells in the area, in going through the wall of bag 28, is not yet focused, so that the power density is so low that the bag is not destroyed or damaged.

Light beam 61, or beams 61 and 62, can also be focused on a stationary point of image plane 21, and the blood or blood cells flow through the areas of the point, as is known in connection with the so-called flow chambers.

Figure 2:
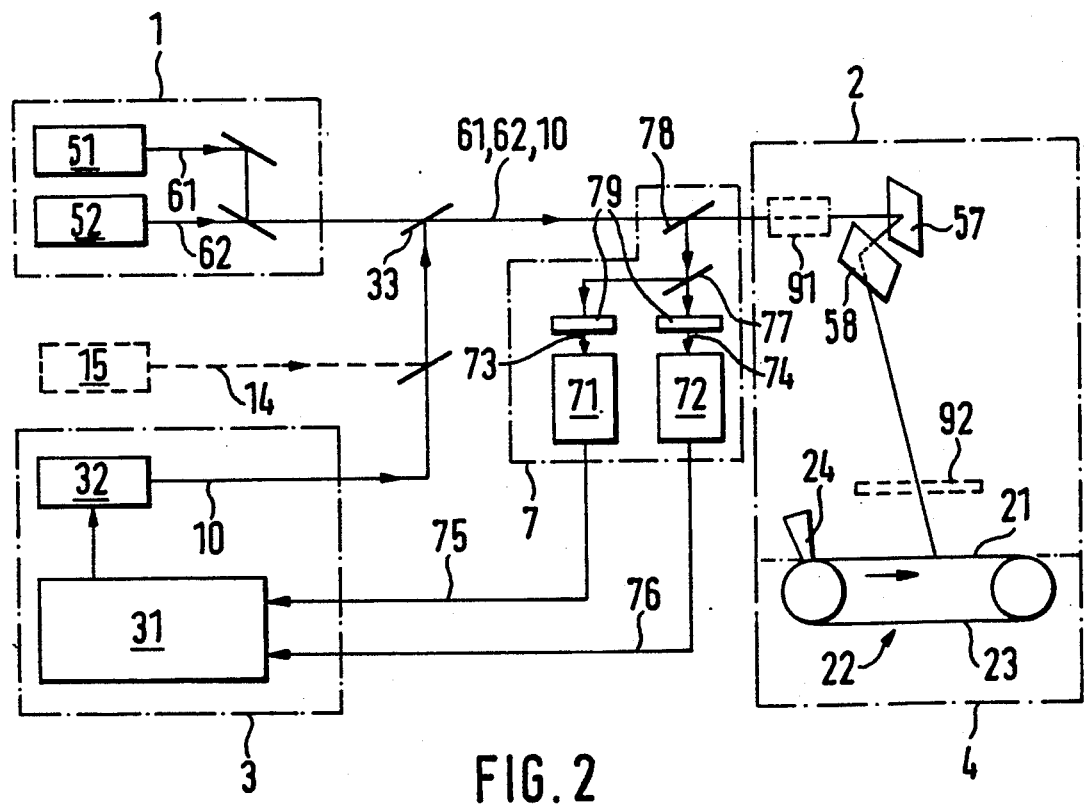
FIG. 2 is a detailed block diagram of a preferred embodiment of the present invention.

Referring now back to FIG. 2, it is seen that the detector unit 7 includes sensors 71 and 72 corresponding, illustratively, to the pair of light sources 61 and 62. These sensors receive the fluorescence emitted by the cells 73 and 74, or radiation reflected or scattered on the cells, and generate detector signals 75 and 76 upon receiving a certain fluorescence or certain radiation. Preferably the fluorescence emitted by the cells or the radiation reflected on the cells is fed back by the optical system of scanning device 2, and the fluorescence signals or reflected light signals 73 and 74 are suitably supplied by beam dividers 77 and 78 from the beam path of the optical system to sensors 71 and 72. But it is also possible to provide sensors 71 and 72 of detector unit 7 at the side of image plane 21. This is especially suitable in the case of analysis of the radiation scattered on the cells. Additionally, glass fibers can also be used for guiding the various light beams, as is known in the art.

Detector signal 75, or detector signals 75 and 76, are fed to a control device 31 within the active unit 3, in which a central processing unit (CPU) is involved, to generate an activation signal from the detector signal(s). Preferably, photomultiplier tubes are used as sensors 71 and 72, upstream from which one or more filters 79 are installed. These filter(s) pass only one wavelength, which corresponds precisely to the emitted fluorescence or other radiation of interest.

The activation signal from the control device 31 is fed to a light source 32 of active unit 3, which produces the power light beam 10 with the power and wavelength which are suitable for destruction or inactivation of the cells. For this light source 32, a laser source, especially an argon laser, is preferably involved. It is also possible to produce UV light by this light source 32. Power light beam 10 of light source 32 is supplied by a beam divider 33 into the beam path of the optical system of scanning device 2.

In an alternate embodiment, instead of the aforementioned light source 51 with low power, and the light source 32 with high power, a single light source 15 can also be provided. This single light source 15 normally produces a light beam 14 with low power which is harmless to the cells, and the power of this light beam 14 in the presence of the activation signal from the control device 31 can momentarily be so increased that it is sufficient for destruction or inactivation of cells. After a preset period, which may be from about 30 to 40 nsec, the energy of light beam 14 in each case is again reduced to the low energy level and the scanning process is continued. For the light source 15, a known laser device of the so-called acoustooptic cavity dumping type may be used; which in the presence of the activation signal can produce in a rise time of 7 nsec, a high-energy pulse of 36 nsec.

Possible solutions are explained below by which even with great deflections of the focal spot of light beam 61, or beams 61, 62 and 10 in the image plane 21, a correction of the spherical aberration is achieved. A novel idea for solving this problem consists in the use of a lens rotating on a disc, which is synchronized with the movement of deflection mirrors 57 and 58 or with the control of the alternate electrooptical deflectors. FIG. 5 shows such an arrangement. A disk 81 eccentrically carrying a lens 83 is so rotated, and deflection mirrors 57 and 58 (or the electrooptical deflectors) were so driven or controlled, that it is always assured that light beams 61, and 62 or 10, all guided by the common optical system of scanning device 2, always accurately follow the rotation of lens 83 during a preset period. Since the lens 83 describes a circular path, a deflection in the X-Y direction is necessary. Then in the image plane 21 a circular deflection line 84 of the focal spot or spots occurs. Scanning in the other direction (Y direction) is achieved by the image plane 21 being shifted in the direction of arrow 80 relative to deflection line 84. This occurs, for example, with belt conveyor 22 already mentioned.

Especially preferred in this arrangement is an embodiment in which two lenses 83 and 83' are placed equally distant from the center on a diameter of rotating disk 81 so that with a suitable synchronization of disk 81 and of deflection mirrors 57 and 58 (or of the electrooptical deflectors) a lens 83 or 83' is always rotated exactly into beam 61 and 62 or 10 returned to a beginning position A to follow the beam to an end position E.

Broken line 86 shows the return of the beam from end position E to beginning position A.

It is also possible, instead of rotating disk 81 with lens 83, or lenses 83 and 83', to provide a lens 87 on an oscillating plate 88, which is moved back and forth in a straight line 89, as shown in FIG. 6. In this arrangement, only one deflection mirror or one electrooptical deflector is necessary, which is synchronized with the back and forth movement of plate 88 so that the light beam always goes through lens 87. Straight deflection line 80 then is produced in image plane 21. The advantage of using rotating disk 81 and oscillating plate 88 reside in the fact that lenses of high aperture can be used and thus a great sensitivity can be achieved.

It is further possible for correcting the above described spherical aberration, to place a dynamic lens 91 (as shown in FIG. 2) known in the art, in the beam path such a lens can be shifted in the beam direction as a function of a signal that shows that the focal spot is not in the image plane 21. In this way, it is possible for dynamic lens 91 to be automatically guided so that the focal spot is always exactly in image plane 21. Such dynamic lenses are known, for example, in connection with CD phonographs.

Additionally, in lieu of rotating disk 81, in the beam path ahead of image plane 21 a so-called flat field lens (F lens) can be provided, whose characteristics in the X deflection direction and/or Y deflection direction change so that it is always assured that the deflected focal spot is always in image plane 21. Such a flat field lens is shown diagrammatically as lens 92 in FIG. 2.

Instead of the described laser source producing the power light beam 10, sources producing shock waves can also be used. Moreover, certain cells can be labeled with photolabile substances, which release intracellular poisons if light of suitable wavelength and energy strikes them as beam 10.

In the detection and evaluation of the light reflected or scattered on the blood cells an image or special optically detectable features can be recorded and these can be compared with a previously stored image or previously stored optical features which characterize certain blood cell or cells to be destroyed. In the case of agreement of the detected and stored data, destruction of the blood cells present at the moment can be triggered by generation of the activation signal.

In an illustrative contemporary usage of the present invention, a possible AIDS therapy is described. T4 lymphocytes infected with RTLV-III viruses incorporate (after activation with Interlencin I and antigen) virus protein in the T4 cell membrane. Therefore, it seems possible selectively to label the infected cells with fluorescence labeled antibodies relative to the virus proteins. Illustratively, an assumption is made that 5 liters of blood, which contains 8000 leukocytes per microliter, is treated. This means that $5 \times 10^6 \times 8000 = 4 \times 10^{10}$ leukocytes are in 5 liters of blood. It is further assumed that 50%, i.e., $2 \times 10^{10}$, are T-lymphocytes. The blood cells have a diameter of about 10 microns. This means that the focal spot of laser beam 10 used for selective cell destruction is to have a diameter of about 10 microns. Such focal spot sizes are easily attainable.

If the assumption is that $10^{10}$ cells are closely pressed against one another, an area of about $10^{10} \times 10 \times 10^{-6} \times 10 \times 10^{-6} = 1$ m$^2$ is covered. Each cell is to be selectively illuminated within 10,000 sec., i.e., about 2.7 hours. This corresponds to a frequency of $10^{10}$ cells/$10^4$ equal to $10^6$ hertz. For the scanning of a blood cell about 1 microsecond is available which is technically possible. During the scanning, the cells can be cooled, for example to 4° C., by a moderating device, not shown. Thus, e.g., the fluorescence is stabilized.

We claim:

1. A system for selective destructive or inactivation of cells, wherein planar arrays of cells are successively illuminated with a lower powered light beam produced by at least one light source and the radiation of particular cells responsive to said illumination enables a higher powered beam routed via a substantially common optical path to accomplish said destruction or inactivation in a near simultaneous manner, said system comprising:
   (a) means defining an image plane for groups of cells;
   (b) at least one laser light source for producing at least a first light beam to illuminate groups of cells positioned in said image plane;
   (c) scanning means for directing said at least first light beam within said image plane to successively illuminate said groups of cells in the image plane;
   (d) at least one optical detector for sensing predetermined radiations occurring from a particular cell of said groups of cells at a particular point of said scanning means in response to said illumination, and for producing at least one detector signal responsive to said sensed predetermined radiations;
   (e) control means operating in response to said detector signal to enable a second light beam to be directed through said scanning means to said particular point, wherein the power level of said second light beam is sufficient to destroy or inactivate said particular cell;
   (f) said control means effecting activation of said second light beam before said scanning means has moved appreciably from said particular point;
   (g) said first light beam and said second light beam being formed by a single light source; and
   (h) wherein said control means permits a single light beam to be switched from a low power harmless to cells to a higher power harmful to cells upon detector signal production wherein said scanning means comprises mirrors for deflecting said light beams in X-Y directions of a Cartesian coordinate system.

2. The system according to claim 1 wherein said single light source laser is an argon laser.

3. The system according to claim 1 wherein one of said deflection mirrors deflects said light beams in a first of said X-Y directions of said image plane and said image plane is movable in a second of said directions.

4. The system according to claim 3 wherein said scanning means further comprise a dynamic lens positioned in front of said mirrors for correction of spherical aberration in said beams at said image plane.

5. The system according to claim 4 wherein said scanning means further comprise a flat field lens for correction of the spherical aberration between said image plane and said mirrors.

6. The system according to claim 1 wherein said image plane corresponds to an inside bottom surface of a vessel in which the cells are placed.

7. The system according to claim 1 wherein said image plane is formed by at least one partial area of the surface of a belt of a conveyor.

8. The system according to claim 7 wherein said belt consists of a transparent material, and said optical detector is placed on the side of the belt opposite to said image plane.

9. The system according to claim 7 wherein said belt includes outwardly projecting side walls on its sides so that a duct is formed for receiving the cells.

10. The system according to claim 1 wherein a cell feed device feeds blood cells taken from a patient to said image plane.

11. The system according to claim 10, wherein upstream from the cell feed device there is connected to the cell feed device a preselector separating blood cells and preselected cells said patient's blood circulation.

12. The system according to claim 1 wherein said scanning means further comprises a rotatable lens eccentrically fastened to a rotatable disk which may be moved in synchronization with said deflection mirrors.

13. The system according to claim 1 wherein said scanning means includes in front of said image plane an oscillation plate with a lens whereby said oscillation plate can be moved in one direction while oscillating in synchronization with an oscillation of one of said deflection mirrors.

* * * * *